United States Patent
Dhuppad et al.

(10) Patent No.: US 10,709,663 B2
(45) Date of Patent: Jul. 14, 2020

(54) MUPIROCIN CREAM IN PUMP DEVICE

(71) Applicant: Glenmark Pharmaceuticals Inc., USA, Mahwah, NJ (US)

(72) Inventors: Ulhas Dhuppad, Nashik (IN); A. V. V. P. S. Raghuveer, East Godavari District (IN); Ram Reddy Patlolla, Hyderabad (IN); Atul Chopade, Mumbai (IN); Madhusudhan Bommagani, Navi Mumbai (IN); Rahul Kapse, Navi Mumbai (IN); Sushrut Kulkarni, Navi Mumbai (IN)

(73) Assignee: GLENMARK PHARMACEUTICALS, INC., USA, Mahwah, NJ (US)

( * ) Notice: Subject to any disclaimer, the term of this patent is extended or adjusted under 35 U.S.C. 154(b) by 0 days.

(21) Appl. No.: 16/352,613

(22) Filed: Mar. 13, 2019

(65) Prior Publication Data

US 2019/0224119 A1 Jul. 25, 2019

(51) Int. Cl.
| | |
|---|---|
| A61M 35/00 | (2006.01) |
| A61K 9/06 | (2006.01) |
| A61K 9/00 | (2006.01) |
| A61K 31/351 | (2006.01) |
| A61K 47/10 | (2017.01) |
| A61K 47/36 | (2006.01) |
| A61K 47/14 | (2017.01) |
| A61K 47/34 | (2017.01) |
| A61K 47/44 | (2017.01) |
| A61K 47/06 | (2006.01) |

(52) U.S. Cl.
CPC .............. *A61K 9/06* (2013.01); *A61K 9/0014* (2013.01); *A61K 31/351* (2013.01); *A61K 47/10* (2013.01); *A61K 47/14* (2013.01); *A61K 47/34* (2013.01); *A61K 47/36* (2013.01); *A61K 47/44* (2013.01); *A61M 35/003* (2013.01); *A61K 47/06* (2013.01)

(58) Field of Classification Search
CPC ...... A61K 9/06; A61K 9/0014; A61K 31/351; A61K 47/10; A61K 47/14; A61K 47/34; A61K 47/36; A61K 47/44; A61M 35/003
See application file for complete search history.

(56) References Cited

U.S. PATENT DOCUMENTS

| | | | |
|---|---|---|---|
| 4,511,068 A | 4/1985 | Bossina | |
| 6,025,389 A | 2/2000 | Zimmerman | |
| 6,121,314 A | 9/2000 | Richter et al. | |
| 2010/0323998 A1 | 12/2010 | Dhuppad et al. | |
| 2014/0371690 A1 | 12/2014 | Sprada et al. | |
| 2015/0314115 A1 | 11/2015 | Nordsiek et al. | |
| 2017/0252763 A1* | 9/2017 | Ransch | A45D 33/26 |

FOREIGN PATENT DOCUMENTS

WO WO-2008007182 A2 1/2008

OTHER PUBLICATIONS

Prescribing information for Bactroban (mupirocin calcium) cream, Mar. 2017.

(Continued)

*Primary Examiner* — Kai H Weng
(74) *Attorney, Agent, or Firm* — Blank Rome LLP

(57) ABSTRACT

The present invention relates to a mupirocin topical pharmaceutical composition in a pump device, and its use for dispensing predetermined quantities of mupirocin for treating skin lesions.

6 Claims, 2 Drawing Sheets

(56) References Cited

OTHER PUBLICATIONS

Prescribing information for mupirocin cream (Glenmark Pharmaceuticals), Jul. 2017.
International Search Report issued in PCT/US19/22116 dated Jun. 6, 2019.
Bikowski, Antimicrobial Wound Management in the Emergency Department: An Educational Supplement; The Journal of Emergency Medicine, 1999, 17:1:197-206.

* cited by examiner

MUPIROCIN CREAM IN PUMP DEVICE

This application claims the benefit of Indian Patent Application No. 201821039387, filed Oct. 17, 2018, which is hereby incorporated by reference.

FIELD OF THE INVENTION

The present invention relates to a mupirocin topical pharmaceutical composition in a pump device, and its use for dispensing predetermined quantities of mupirocin for treating skin lesions.

BACKGROUND OF THE INVENTION

Mupirocin cream 2% (available as Bactroban® cream) is indicated for the treatment of secondarily infected traumatic skin lesions (up to 10 cm in length or 100 $cm^2$ in area) due to susceptible isolates of *Staphylococcus aureus* (*S. aureus*) and *Streptococcus pyogenes* (*S. pyogenes*). Mupirocin is an antibiotic. It works by stopping the growth of *Staphylococcus aureus* (*S. aureus*) and *Streptococcus pyogenes* (*S. pyogenes*).

Nowadays antimicrobial resistance has been described as a "crisis for the health and wealth of nations". One of the key strategies to mitigate this public health crisis is to ensure that existing antimicrobials are used responsibly and judiciously. The article "A bug in the ointment: topical antimicrobial usage and resistance in New Zealand" published by New Zealand Medical Association in journal NZMJ, 4 Dec. 2015, Vol 128; No 1426, discloses the threat of antimicrobial resistance from mupirocin.

U.S. Pat. No. 6,025,389 discloses a pharmaceutical composition comprising a cream base and a therapeutic agent, such as mupirocin, and a method for treating a bacterial infection using the composition. WO 2008/007182 discloses a topical pharmaceutical composition comprising (a) a therapeutically effective amount of mupirocin or a pharmaceutically acceptable salt or ester thereof and (b) one or more esters of a fatty acid. U.S. Pat. No. 6,025,389 and WO 2008/007182 are silent on the drawbacks associated with dispensing of mupirocin cream.

The dispensers known in art such as aluminium tubes are generally simple and convenient to use, but the amount of drug dispensed cannot be precisely controlling resulting in significant waste. There are several other disadvantages associated with providing mupirocin cream to a patient in an aluminium tube. Aluminium tubes pre-filled with a topical mupirocin cream are, for example, messy, difficult and clumsy to use, and more importantly imprecise. These known drawbacks can lead to needless product waste, overdosing, inadequate dosing, failed compliance, passive (unintended) transfer to other areas of the patients' bodies, such as the eyes, ears, nose and mouth. All of these may result in antimicrobial resistance from mupirocin against *Staphylococcus aureus* (*S. aureus*) and *Streptococcus pyogenes* (*S. pyogenes*). Over-application of medication increases the potential for application-site reactions and signs and symptoms of skin irritation, at least in some patients. Thus, dosing inconsistencies and product waste associated with aluminium tubes of mupirocin are problematic, common and a cause for concern.

In yet another drawback, aluminium tubes can be very difficult and cumbersome to use, especially when elderly patients are involved. Opening the aluminium tube and dispensing the cream to "only" a targeted area without excessive handling or passive transfer can be a challenge to those patients inflicted with limited dexterity, crippling arthritis, vision loss or visual acuity loss, which are commonly observed in elderly patients.

In still another drawback associated with aluminium tubes, mupirocin cream degradants may develop over time as a result of storage in an aluminium tube. This drawback may cause an adverse effect on overall efficacy and/or stability of the mupirocin cream formulations packaged within aluminium tube. Thus, there is an unmet need for a simple, safe, clean, easy-to-use, compact, reliable system for dispensing topical mupirocin cream.

SUMMARY OF THE INVENTION

In accordance with an aspect of the present invention, there is provided a dispensing system comprising a topical pharmaceutical composition of mupirocin or a salt thereof in a pump device. In one embodiment, the topical pharmaceutical composition is in the form of a cream.

Another embodiment is a mupirocin dispensing system comprising:
  (a) a topical pharmaceutical composition of mupirocin or a salt thereof (such as a mupirocin cream); and
  (b) a pump device (such as an airless pump device).

In one embodiment, the topical pharmaceutical composition of mupirocin comprises mupirocin or a salt thereof, a mineral oil, a preservative, one or more fatty alcohols or fatty esters, a polyoxyethylene ether or ester surfactant, xanthan gum and water. In one preferred embodiment, the topical pharmaceutical composition is in the form of a cream.

In one embodiment, the airless pump device comprises a substantially tubular main body portion and a manually-operated airless pumping device mounted on the main body portion. The main body portion of the pump device defines a storage chamber. The pump device defines a dispensing duct which terminates in a discharge orifice. The airless pump device may optionally include a cap or cover for sealing or covering the discharge orifice. In another embodiment, the airless pumping device defines a dispensing duct which terminates in a self-sealing discharge orifice.

Another embodiment is a dispensing system comprising (a) a topical pharmaceutical composition of mupirocin or a salt thereof (e.g., a mupirocin cream), and (b) an airless pump device, where the airless pump device comprises a substantially tubular main body portion and a manually-operated airless pumping device mounted on the main body portion. The main body portion of the pump device defines a storage chamber. The pump device defines a dispensing duct which terminates in a discharge orifice. The airless pump device may optionally include a cap or cover for sealing or covering the discharge orifice. The topical pharmaceutical composition is disposed at least partially within the storage chamber defined in the main body portion of the pump device. The pump device is constructed such that manual operation of the airless pump device causes a portion of the topical pharmaceutical composition to be withdrawn from within the storage chamber through the dispensing duct thereby dispensing, per actuation, a predefined, uniform and precisely measured unit dose amount of the topical pharmaceutical composition. In one embodiment, the predefined, uniform and precisely measured unit dose amount of the topical pharmaceutical composition ranges from about 0.34 to about 0.45 g, such as from about 0.40 to about 0.45 g.

The dispensing system of the present invention affords patients with the unique advantage of applying a consistent, precisely measured and uniform unit-dose of mupirocin from a clean, safe, easy and simple to use, compact and reliable dispensing device. The dispensing system minimizes (a) imprecise or inconsistent dosing amounts, i.e., under-dosing or over-dosing, (b) unwanted passive transfer of the dispensed topical mupirocin due to improper handling and poor application technique, and (c) wastage of mupirocin, each of which can contribute to poor patient compliance, antibiotic resistance and less effective, if not ineffective, topical mupirocin therapy.

Another embodiment is a dispensing system comprising
(a) a topical pharmaceutical composition of mupirocin or a salt thereof, and
(b) an airless pump device, wherein the airless pump device comprises
  i. a lower subassembly that has a substantially tubular body portion that defines an elongated interior storage chamber into which a take-up piston element is slidably disposed and
  ii. an upper subassembly mounted upon the lower subassembly and includes a dispensing head dispensing having an internal fluid passage or discharge duct formed therein which terminates in an outlet and an airless pumping mechanism
wherein the pump device is constructed such that manual operation of the airless pump device causes a portion of the topical pharmaceutical composition to be withdrawn from within the storage chamber through the dispensing duct thereby dispensing, per actuation, a predefined, uniform and precisely measured unit dose amount of the topical pharmaceutical composition.

Another embodiment is a dispensing system comprising
a. a pump device;
b. a topical cream composition comprising:
  i. 2.365% by weight of mupirocin (e.g., mupirocin calcium);
  ii. 1% by weight of benzyl alcohol;
  iii. 50.6% by weight of a mineral oil;
  iv. 0.5% by weight of phenoxyethanol;
  v. 0.215% by weight of xanthan gum;
  vi. 6% by weight of a polyoxyethylene ether or ester surfactant;
  vii. 5% by weight of glyceryl monostearate; and
  viii. water
wherein said pump device delivers a unit dose amount about 300-500 mg of mupirocin composition per actuation.

One embodiment is a method of treating a bacterial infection in a patient in need thereof by (i) dispensing the topical composition from a dispensing system described herein, and (ii) topically applying the dispensed topical composition on the patient.

Another embodiment is a method for treating secondarily infected traumatic skin lesions due to susceptible isolates of *Staphylococcus aureus* (*S. aureus*) and *Streptococcus pyogenes* (*S. pyogenes*) with the dispensing system comprising:
(a) a topical pharmaceutical composition of mupirocin comprising:
  i. 2.365% by weight of mupirocin (e.g., mupirocin calcium);
  ii. 1% by weight of benzyl alcohol;
  iii. 50.6% by weight of a mineral oil;
  iv. 0.5% by weight of phenoxyethanol;
  v. 0.215% by weight of xanthan gum;
  vi. 6% by weight of a polyoxyethylene ether or ester surfactant;
  vii. 5% by weight of glyceryl monostearate; and
  viii. water and (b) an airless pump device, where the airless pump device comprises a substantially tubular main body portion and a manually-operated airless pumping device mounted on the main body portion. The main body portion of the pump device defines a storage chamber. The pump device defines a dispensing duct which terminates in a discharge orifice. The topical pharmaceutical composition is disposed at least partially within the storage chamber defined in the main body portion of the pump device. The pump device is constructed such that manual operation of the airless pump device causes a portion of the topical pharmaceutical composition to be withdrawn from within the storage chamber through the dispensing duct thereby dispensing unit dose amount of about 300-500 mg of mupirocin composition per actuation. The method includes dispensing the topical pharmaceutical composition and applying the topical pharmaceutical composition to the target area (e.g., skin lesion) of the patient.

Another embodiment relates to a method for treating secondarily infected traumatic skin lesions due to susceptible isolates of *Staphylococcus aureus* (*S. aureus*) and *Streptococcus pyogenes* (*S. pyogenes*) with the dispensing system, wherein the chances of antibiotic resistance of mupirocin is reduced. The method includes dispensing the topical pharmaceutical composition and applying the topical pharmaceutical composition to the target area (e.g., skin lesion) of the patient.

In another embodiment, the topical pharmaceutical composition comprises:
(a) 1 to 3% by weight of mupirocin or a salt thereof (e.g., mupirocin calcium);
(b) 40 to 60%, preferably 45 to 55%, by weight of a mineral oil;
(c) 2 to 15%, preferably 3 to 10%, by weight of one or more fatty alcohols or fatty esters;
(d) 4 to 8%, preferably 5 to 7%, by weight of a polyoxyethylene ether or ester surfactant; and
(e) 20 to 35%, preferably 25 to 35%, by weight of water, based upon 100% total weight of composition.

Preferably, the composition is in the form of a cream.

Another embodiment is a dispensing system comprising:
(a) a topical pharmaceutical composition of mupirocin or a salt thereof; and
(b) a pump device, wherein
said pump device delivers a unit dose amount of about 0.1 to 1 gram of mupirocin composition per actuation, preferably about 200-600 mg of mupirocin composition per actuation, more preferably about 300-500 mg of mupirocin composition per actuation.

Another embodiment relates to a dispensing system comprising
a. a pump device;
b. a stable topical cream composition comprising:
  i. 2.365% by weight of mupirocin or a salt thereof;
  ii. 1% by weight of benzyl alcohol;
  iii. 50.6% by weight of a mineral oil;
  iv. 0.5% by weight of phenoxyethanol;
  v. 0.215% by weight of xanthan gum;
  vi. 6% by weight of a polyoxyethylene ether or ester surfactant;
  vii. 5% by weight of glyceryl monostearate; and
  viii. Water
wherein total weight of said composition in said pump device is in range of about 25 gm to about 50 gm;

wherein said pump device delivers unit dose amount of about 200-600 mg of mupirocin composition per actuation, more preferably about 300-500 mg of mupirocin composition per actuation.

Another embodiment is a method of applying a topical mupirocin pharmaceutical composition to a patient with a dispensing system comprising an airless pump device to a patient in need thereof, where said method comprises (1) actuating a primed dispensing system pre-filled with a topical mupirocin pharmaceutical composition (such as one of those described herein) to dispense therefrom an effective precisely measured unit dose amount of the topical mupirocin pharmaceutical composition and (2) applying the dispensed unit dose amount to a treatment area on the patient. In one embodiment, the topical mupirocin pharmaceutical composition is applied to the treatment area three (3) times daily for 10 days or longer. This method can be used with any of the mupirocin compositions, pump devices, and dispensing systems described herein.

The percentages for the topical pharmaceutical compositions described herein are based on the total weight of the composition unless otherwise indicated. The topical pharmaceutical composition may also include minor amounts (such as up to about 10%) of additives, such as viscosity modifiers, for example, xanthan gum, and preservatives, such as phenoxyethanol or benzyl alcohol, including any combination of any of the foregoing.

It should be understood by those versed in this art that the pump device can be pre-filled with any suitable topical mupirocin pharmaceutical composition, such as a cream, an ointment, a lotion, a balm, or a salve, that can be effectively dispensed therefrom without departing from the purpose or scope of the present invention. Thus, when the pump device is described as being pre-filled with a topical mupirocin pharmaceutical cream, such description is done so for exemplary purposes without the intent to be bound to any particular topical mupirocin dosage form or formulation.

It is envisioned that in certain embodiments the pump device includes a take-up piston which is slidably disposed within the substantially tubular main body portion so as to partially define the storage chamber. The take-up position moves axially towards the pumping device when the pumping device is manually operated, so as to reduce the volume of the fluid storage chamber by an amount which is equivalent to the volume of the topical pharmaceutical composition dispensed from the dispensing system, i.e., the unit dose amount. In constructions wherein the take-up piston defines a portion of the storage chamber, it can be positioned during assembly to establish the desired volume of the storage chamber. For example, if it is desired to pre-fill the dispensing device with 45 g of mupirocin cream, the piston can be initially positioned during the filling operation at a distance from the top of the main body portion of the dispensing package such that the volume of the fluid storage chamber corresponds to the volume required to hold 45 g of mupirocin cream. Alternatively, if 30 grams of cream is to be stored, the piston can be moved the appropriate distance towards the top of the main body portion of the dispensing package to accommodate 30 g of mupirocin cream, if it is desired to pre-fill the dispensing device with 15 g of mupirocin cream, the piston can be initially positioned during the filling operation at a distance from the top of the main body portion of the dispensing package such that the volume of the fluid storage chamber corresponds to the volume required to hold 15 g of mupirocin cream. Alternatively, if 7.5 grams of cream is to be stored, the piston can be moved the appropriate distance towards the top of the main body portion of the dispensing package to accommodate 7.5 g of mupirocin cream. Of course, it should be appreciated by those versed in this art that the mupirocin pump device of the present invention contemplates functional storage chambers that can accommodate any desired volume of topical pharmaceutical composition, so long as the objectives of the present invention are not defeated.

Another embodiment is a dispensing system for treating secondarily infected traumatic skin lesions due to susceptible isolates of *Staphylococcus aureus* (*S. aureus*) and *Streptococcus pyogenes* (*S. pyogenes*) which includes, inter alia, a dispensing system that is pre-filled with a topical mupirocin pharmaceutical composition, such as a mupirocin cream. The dispensing system includes a pump device comprising a lower subassembly and an upper subassembly. The lower subassembly has a tubular body portion that defines an elongated interior storage chamber into which a take-up piston element is slidably disposed. The upper subassembly is mounted upon the lower subassembly and includes a dispensing head and an airless pumping mechanism. The dispensing head has an internal fluid passage or discharge duct formed therein which terminates in an outlet. The dispensing head also includes a finger-operated actuator which is operatively associated with the airless pumping mechanism. The dispensing package may further include a cap to seal or cover the dispensing head or nozzle.

The topical mupirocin pharmaceutical composition, e.g., mupirocin cream, is disposed at least partially within the storage chamber defined in the tubular body portion of the lower subassembly of the dispensing package. Operation of the finger-operated actuator causes the airless pumping mechanism to withdraw a portion of the mupirocin cream from within the interior chamber and to dispense the mupirocin cream into the internal fluid passage formed thereby discharging a predetermined final unit dose of mupirocin cream from the dispensing head.

In certain preferred embodiments, the take-up piston is disposed within the tubular body portion so as to partially define the storage chamber. The take-up position is arranged such that it moves axially towards the pumping device when the pumping device is manually operated, so as to reduce the volume of the storage chamber by an amount which is equivalent to the volume of mupirocin cream dispensed from the dispensing package, i.e., the unit dose amount. This provides the predetermined amount of mupirocin cream while minimizing wastage.

In another embodiment, the pump device has a substantially tubular main body portion and a manually-operated airless pumping mechanism mounted on the main body portion. The main body portion of the pump device defines a storage chamber which is in fluid communication with a dispensing duct which is defined in the pumping device and that terminates in a discharge orifice.

Utilizing such dispensing system that dispenses precise effective unit dose amount of the formulation allows the patient to repeatedly and consistently dispense and applied precisely measured effective unit dose amounts over the course of treatment. Dispensing the mupirocin cream composition from an airless pumping device allows subsequent actuations of the device to dispense an effective unit dose amount to improve consistency and effectiveness of treatment, the unit-dose having been protected from exposure to air, oxidation and/or contaminants to remain effective. Providing these features are especially useful in improving patient compliance and patient outcomes, particularly given the challenges associated with mupirocin treatments.

The application of mupirocin cream composition by a patient can be difficult due to a number of challenges which may lead to sub-optimal results, reduced efficacy or antimicrobial resistance. Since mupirocin is an antibiotic, it is desirable to avoid unintended or overexposure to mupirocin composition, particularly with skin areas that are not targeted for treatment. Typically, application of mupirocin cream to a targeted area requires applying thin layer of cream to the targeted area. Given the ability of the composition to absorb into the skin and the desire to avoid unnecessary contact, the entire unit dose amount should be applied to clean cotton wool pad or gauze swab and rubbed in to the targeted area. Reapplication and excessive handling of the formulation may result in absorption in unintended areas or overexposure through the fingertips.

The present invention is also directed to methods for treating secondarily infected traumatic skin lesions due to susceptible isolates of *Staphylococcus aureus* (*S. aureus*) and *Streptococcus pyogenes* (*S. pyogenes*) with the dispensing system pre-filled with a topical mupirocin pharmaceutical composition. One embodiment is a method for treating secondarily infected traumatic skin lesions due to susceptible isolates of *Staphylococcus aureus* (*S. aureus*) and *Streptococcus pyogenes* (*S. pyogenes*) in a patient in need thereof comprising applying to the patient the topical mupirocin pharmaceutical composition dispensed from the dispensing system of the present invention. In one embodiment, the topical mupirocin pharmaceutical composition is applied in accordance with an effective treatment regimen, such as one of those treatment regimens described herein. For example, the method of application may comprise (1) actuating a primed dispensing system pre-filled with a topical mupirocin pharmaceutical composition (such as one of those described herein) to dispense therefrom an effective precisely measured unit dose amount of the topical mupirocin pharmaceutical composition, where the unit dose amount dispensed per each actuation is the same effective precisely measured unit dose amount for consistent dose application over the course of the treatment, and (2) applying the dispensed unit dose amount to a treatment area.

The topical pharmaceutical composition may be prepared by:

(a) adding xanthan gum to water (e.g., purified water) to form an aqueous phase;

(b) heating a mixture of mineral oil, polyoxyl 20 cetostearyl ether and glyceryl monostearate to form an oil phase;

(c) adding benzyl alcohol and phenoxyethanol to the mixture of step (b);

(d) adding mupirocin or a salt thereof to the oil phase to form a uniform dispersion;

(e) adding the aqueous phase to the oil phase to form the pharmaceutical composition.

The dispensing system of the present invention uniquely affords a proper, safe, convenient, easy and advantageous way to dispense and apply topical mupirocin pharmaceutical compositions to improve patient compliance and to more effectively treat secondarily infected traumatic skin lesions due to susceptible isolates of *Staphylococcus aureus* (*S. aureus*) and *Streptococcus pyogenes* (*S. pyogenes*), while mitigating, if not eliminating, the drawbacks associated with the use of aluminium tubes containing topical mupirocin formulations.

The above summary of the present invention is not intended to describe each disclosed embodiment or every implementation of the present invention. The description and examples that follow more particularly exemplify illustrative embodiments. In several places throughout the specification, guidance is provided through lists of examples, which examples can be used in various combinations. In each instance, the recited list serves only as a representative group and should not be interpreted as an exclusive list.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

Figure 1:
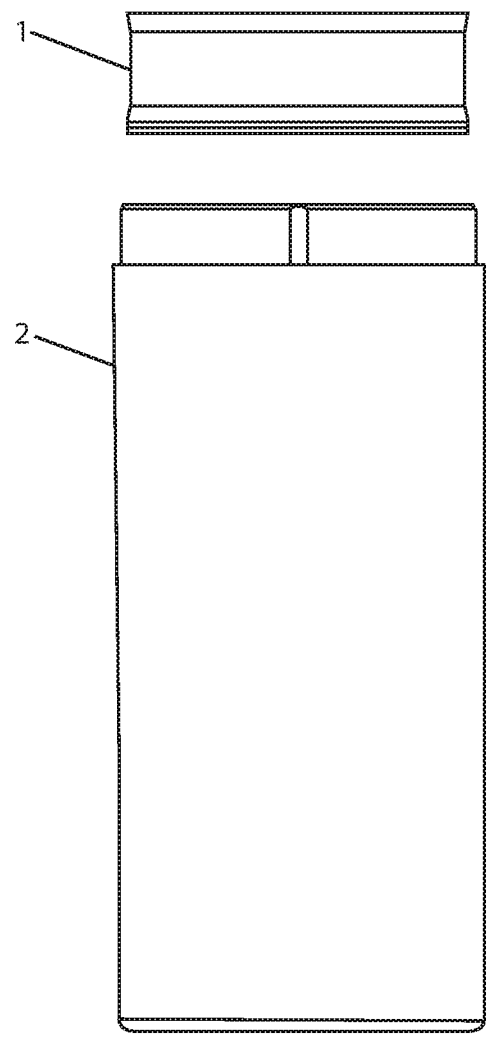
FIG. 1 shows the lower subassembly of a pump device of the present invention.

The figures only represent embodiments of the present invention. The embodiments are meant only for the purpose of illustration of the present invention.

Persons skilled in the art will appreciate that elements in the figures are illustrated for simplicity and clarity and may have not been drawn to scale. For example, the dimensions of some of the elements in the figure may be exaggerated relative to other elements to help to improve understanding of various exemplary embodiments of the present disclosure. Throughout the drawings, it should be noted that like reference numbers are used to depict the same or similar elements, features, and structures.

SCHEDULE OF REFERENCE NUMERALS

Figure 2:
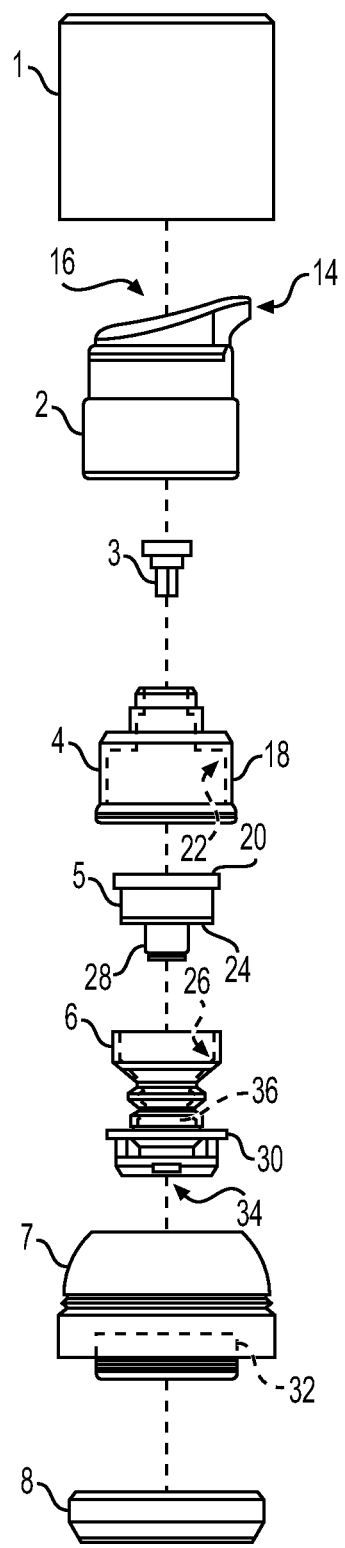
FIG. 2 shows the upper subassembly of a pump device of the present invention.

| FIG. 1 | FIG. 2 |
|---|---|
| 1. Piston | 1. Cap |
| 2. Container/Main Body | 2. Actuator (Outer) |
| | 3. Valve |
| | 4. Actuator (Inner) |
| | 5. Reduction Plug |
| | 6. Bellow |
| | 7. Adapter |
| | 8. Adapter Ring |

DETAILED DESCRIPTION OF THE INVENTION

Disclosed herein are detailed descriptions of specific embodiments of the devices, systems and methods for storing and dispensing unit doses of a topical mupirocin pharmaceutical composition, such as mupirocin cream. It will be understood that the disclosed embodiments are merely examples of the way in which certain aspects of the invention can be implemented and do not represent an exhaustive list of all of the ways the invention may be embodied. Indeed, it will be understood that the pump systems, devices, methods and package assemblies described herein may be embodied in various and alternative forms. The figures are not necessarily to scale and some features may be exaggerated or minimized to show details of particular components. Well-known components, materials or methods are not necessarily described in great detail in order to avoid obscuring the present disclosure. Any specific structural and functional details disclosed herein are not to be interpreted as limiting, but merely as a basis for the claims and as a representative basis for teaching one skilled in the art to variously employ the invention.

Thus, by way of illustrating and providing a more complete appreciation of the present invention and many of the attendant advantages thereof, the following detailed description and examples are given concerning the novel methods and compositions.

Unless otherwise indicated, all numbers expressing quantities, ratios, and numerical properties of ingredients, reaction conditions, and so forth used in the specification and claims are to be understood as being modified in all instances by the term "about". All parts, percentages, ratios, etc. herein are by weight unless indicated otherwise.

As used herein, the singular forms "a" or "an" or "the" are used interchangeably and intended to include the plural forms as well and fall within each meaning, unless expressly stated otherwise. Also as used herein, "at least one" is intended to mean "one or more" of the listed elements. Singular word forms are intended to include plural word forms and are likewise used herein interchangeably where appropriate and fall within each meaning, unless expressly stated otherwise. Except where noted otherwise, capitalized and non-capitalized forms of all terms fall within each meaning.

The term "comprising" as used herein means that steps and ingredients other than those specifically mentioned can be added. This term encompasses the terms "consisting of" and "consisting essentially of." The compositions and methods of the present invention can comprise, consist of, and consist essentially of the essential elements and limitations of the invention described herein, as well as any of the additional or optional ingredients, components, steps, or limitations described herein.

The mupirocin in the topical pharmaceutical composition (such as a cream) may in any form, such as its free form or a salt form. In one preferred embodiment, the mupirocin is in the form of its calcium salt (e.g., mupirocin calcium, which is a hemicalcium salt of mupirocin), such as a dihydrate thereof. For example, the mupirocin may be in the form of its dihydrate crystalline calcium hemi-salt (e.g., ($\alpha$E,2S,3R,4R,5S)-5-[(2S,3S,4S,5S)-2,3-epoxy-5-hydroxy-4-methylhexyl]tetrahydro-3,4-dihydroxy-$\beta$-methyl-2H-pyran-2-crotonic acid, ester with 9-hydroxynonanoic acid, calcium salt (2:1), dihydrate). Suitably, mupirocin or a salt thereof is present in from 1 to 3% by weight of the composition, for example, about 2% (expressed as the weight of the free acid). In another embodiment, the labelled concentration of mupirocin in the topical pharmaceutical composition may be 2% (expressed as the weight of the free acid).

The term "mineral oil" as used herein includes any that is suitable for use in a topical pharmaceutical composition and includes mineral oil USP, light mineral oil NF, liquid paraffin BP and light liquid paraffin BP. The mineral oil known as mineral oil USP is especially suitable.

As a fatty alcohol or fatty ester may be used any of such materials conventionally used in pharmaceutical or veterinary compositions such as myristyl alcohol and glyceryl monostearate. In one embodiment, the fatty ester can contain one or more fatty carbon chains each having from about 4 to about 35 carbon atoms and preferably about 6 to 24 carbon atoms.

The polyoxyethylene ester or ether is one which will function as a non-ionic surfactant. Suitable materials include polyoxyl 20 cetostearyl ethers, such as the material sold under the trade name Cetomacrogol 1000, and polyoxyethylene sorbitan monostearates, such as the material sold under the trade name Polysorbate 60, or polyoxyethylene sorbitan monooleates, as sold under the trade name Tween 80.

The composition of this invention may also include minor amounts (such as up to about 10%) of conventional additives such as viscosity modifiers, for example xanthan gum, and preservatives, such as phenoxyethanol or benzyl alcohol, including mixtures thereof. The composition may optionally include one or more buffering agents to maintain a suitable pH.

In one embodiment, the topical pharmaceutical composition is devoid of stearyl alcohol and/or cetyl alcohol.

One preferred topical pharmaceutical composition comprises from 45% to 55% by weight of a mineral oil, e.g., mineral oil USP); from 3 to 10% by weight of a fatty alcohol or ester, from 5 to 7% of a polyoxyethylene ether or ester surfactant, e.g., a polyethylene glycol monocetyl ether such as cetomacrogol 1000; from 25 to 35% by weight of water and from 1 to 3%, e.g., about 2% by weight (expressed as the weight of free acid) of the calcium salt of mupirocin, in particular the dihydrate salt thereof.

The terms "stable" and "stability" generally indicate that the evolution of the product with time and/or under specific environmental conditions (such as temperature and humidity) has no significant effects on its quality, safety and/or efficacy for a given time period. In one embodiment the compositions according to the invention are considered as stable if at least 90% of the labelled concentration of mupirocin, more preferably at least 95% of the labelled concentration of mupirocin, is found after three months at 40° C. (±2° C.) and 75% (±5%) relative humidity (RH). In another embodiment, the compositions according to the invention are considered as stable if at least 90% of the labelled (or initial) concentration of mupirocin, more preferably at least 95% of the labelled (or initial) concentration of mupirocin, is found after three months at 40° C. (±2° C.) and 75% (±5%) RH, and/or if no substantial change in the appearance, other physical characteristics (such as viscosity and specific gravity) and pH is observed during such a period of time and under such temperature and humidity conditions.

In one embodiment, the topical pharmaceutical composition of mupirocin may be in the form of a cream having a viscosity in the range of about 1.0 to about 7.0 Poise. The viscosity of the topical pharmaceutical composition may be measured at 210 RPM at 25° C. on a Brookfield Cone and Plate Viscometer CAP 2000+(available from Ametek Brookfield of Middleboro, Mass., USA). In another embodiment, the topical pharmaceutical composition has pH of about 6.0 to about 8.0. In another embodiment, the topical pharmaceutical composition of mupirocin has a density of about 0.5 to 1.5 gm/ml more preferably of about 0.75 to 0.95 gm/ml.

The present invention relates to a dispensing system comprising the topical pharmaceutical composition of mupirocin or a salt thereof in a pump device.

One embodiment relates to a dispensing system comprising a topical pharmaceutical composition of mupirocin or a salt thereof in a pump device (as shown in FIG. 2), wherein the topical pharmaceutical composition of mupirocin or a salt thereof is in the form of a cream.

Another embodiment is a dispensing system comprising:
 a. a topical pharmaceutical composition of mupirocin (such as a mupirocin cream); and
 b. a pump device (such as an airless pump device).

Another embodiment is a dispensing system comprising:
 a. a topical pharmaceutical composition of mupirocin; and b. a pump device, wherein said pump device delivers unit dose amount of about 0.1 to 1 gram of mupirocin composition per actuation, preferably about 200-600 mg of mupirocin composition per actuation, more preferably about 300-500 mg of mupirocin composition per actuation.

In one embodiment, the topical pharmaceutical composition of mupirocin comprises mupirocin or a salt thereof, a mineral oil, preservative, one or more fatty alcohols or fatty esters, a polyoxyethylene ether or ester surfactant, xanthan gum and water. In one preferred embodiment, the topical pharmaceutical composition is in the form of a cream.

In one embodiment, the airless pump device comprises a substantially tubular main body portion and a manually-operated airless pumping device mounted on the main body portion. The main body portion of the pump device defines a storage chamber. The pump device defines a dispensing duct which terminates in a discharge orifice. The airless pump device may optionally include a cap or cover for sealing or covering the discharge orifice.

Another embodiment is a dispensing system comprising (a) a topical pharmaceutical composition of mupirocin (e.g., a mupirocin cream), and (b) an airless pump device, where the airless pump device comprises a substantially tubular main body portion and a manually-operated airless pumping device mounted on the main body portion. The main body portion of the pump device defines a storage chamber. The pump device defines a dispensing duct which terminates in a discharge orifice. The airless pump device may optionally include a cap or cover for sealing or covering the discharge orifice. The topical pharmaceutical composition is disposed at least partially within the storage chamber defined in the main body portion of the pump device. The pump device is constructed such that manual operation of the airless pump device causes a portion of the topical pharmaceutical composition to be withdrawn from within the storage chamber through the dispensing duct thereby dispensing, per actuation, a predefined, uniform and precisely measured unit dose amount of the topical pharmaceutical composition.

The dispensing system of the present invention affords patients with the unique advantage of applying a consistent, precisely measured and uniform unit-dose of mupirocin from a clean, safe, easy and simple to use, compact and reliable dispensing device. The dispensing system minimizes (a) imprecise or inconsistent dosing amounts, i.e., under-dosing or over-dosing, (b) unwanted passive transfer of the dispensed topical mupirocin due to improper handling and poor application technique, and (c) wastage of mupirocin, each of which can contribute to poor patient compliance and less effective, if not ineffective, topical mupirocin therapy.

In one embodiment, the topical pharmaceutical composition comprising:
  a. 1 to 3% by weight of mupirocin or a salt thereof;
  b. 40 to 60%, preferably 45 to 55%, by weight of a mineral oil;
  c. 2 to 15%, preferably 3 to 10%, by weight of one or more fatty alcohols or fatty esters;
  d. 4 to 8%, preferably 5 to 7%, by weight of a polyoxyethylene ether or ester surfactant; and
  e. 20 to 35%, preferably 25 to 35%, by weight of water, based upon 100% total weight of composition.
Preferably, the composition is in the form of a cream.

One embodiment relates to a dispensing system comprising
  a. a pump device;
  b. a topical cream composition comprising:
  i. 2.365% by weight of mupirocin or a salt thereof;
  ii. 1% by weight of benzyl alcohol;
  iii. 50.6% by weight of a mineral oil;
  iv. 0.5% by weight of phenoxyethanol;
  v. 0.215% by weight of xanthan gum;
  vi. 6% by weight of a polyoxyethylene ether or ester surfactant;
  vii. 5% by weight of glyceryl monostearate; and
  viii. Water
wherein total weight of said composition in said pump device is in range of about 25 gm to about 50 gm One embodiment relates to a dispensing system comprising
  a) a pump device;
  b) a topical cream composition comprising:
  i. 2.365% by weight of mupirocin or a salt thereof;
  ii. 1% by weight of benzyl alcohol;
  iii. 50.6% by weight of a mineral oil;
  iv. 0.5% by weight of phenoxyethanol;
  v. 0.215% by weight of xanthan gum;
  vi. 6% by weight of a polyoxyethylene ether or ester surfactant;
  vii. 5% by weight of glyceryl monostearate; and
  viii. Water
wherein said pump device delivers unit dose amount of about 200-600 mg of mupirocin composition per actuation, more preferably about 300-500 mg of mupirocin composition per actuation.

One embodiment relates to a dispensing system comprising
  a) a pump device;
  b) a topical cream composition comprising:
  i. 2.365% by weight of mupirocin or a salt thereof;
  ii. 1% by weight of benzyl alcohol;
  iii. 50.6% by weight of a mineral oil;
  iv. 0.5% by weight of phenoxyethanol;
  v. 0.215% by weight of xanthan gum;
  vi. 6% by weight of a polyoxyethylene ether or ester surfactant;
  vii. 5% by weight of glyceryl monostearate; and
  viii. Water
wherein said pump device delivers unit dose amount of about 200-600 mg of mupirocin composition per actuation, more preferably about 300-500 mg of mupirocin composition per actuation. In one preferred embodiment, the total weight of said composition in said pump device is in the range of about 25 gm to about 50 gm.

One embodiment relates to a dispensing system comprising
  a. a pump device;
  b. a stable topical cream composition comprising:
  i. 2.365% by weight of mupirocin or a salt thereof;
  ii. 1% by weight of benzyl alcohol;
  iii. 50.6% by weight of a mineral oil;
  iv. 0.5% by weight of phenoxyethanol;
  v. 0.215% by weight of xanthan gum;
  vi. 6% by weight of a polyoxyethylene ether or ester surfactant;
  vii. 5% by weight of glyceryl monostearate; and
  viii. Water
wherein total weight of said composition in said pump device is in range of about 25 gm to about 50 gm;
wherein said pump device delivers unit dose amount of about 200-600 mg of mupirocin composition per actuation, more preferably about 300-500 mg of mupirocin composition per actuation.

One embodiment relates to a dispensing system comprising
- a pump device;
- a. a stable topical cream composition of mupirocin comprising:
  - i. 1% by weight of benzyl alcohol;
  - ii. 50.6% by weight of a mineral oil;
  - iii. 0.5% by weight of phenoxyethanol;
  - iv. 0.215% by weight of xanthan gum;
  - v. 6% by weight of a polyoxyethylene ether or ester surfactant;
  - vi. 5% by weight of glyceryl monostearate; and
  - vii. water, Wherein (A) total weight of the composition in the pump device is about 25 gm to about 50 gm, and (B) the pump device delivers a unit dose amount of about 200-600 mg of the topical composition per actuation, more preferably about 300-500 mg of the topical composition per actuation.

One embodiment relates to a dispensing system comprising
- a. a pump device;
- b. a stable topical cream composition comprising
  - i. 1 to 3% by weight of mupirocin or a salt thereof;
  - ii. 1% by weight of benzyl alcohol;
  - iii. 50.6% by weight of a mineral oil;
  - iv. 0.5% by weight of phenoxyethanol;
  - v. 0.215% by weight of xanthan gum;
  - vi. 6% by weight of a polyoxyethylene ether or ester surfactant;
  - vii. 5% by weight of glyceryl monostearate; and
  - viii. water wherein the pump device delivers a unit dose amount of about 200 to about 600 mg of the topical composition per actuation, more preferably about 300 to about 500 mg of the topical composition per actuation.

One embodiment relates to a dispensing system comprising
- a pump device;
- b. a stable topical cream composition of mupirocin comprising:
  - i. 1% by weight of benzyl alcohol;
  - ii. 50.6% by weight of a mineral oil;
  - iii. 0.5% by weight of phenoxyethanol;
  - iv. 0.215% by weight of xanthan gum;
  - v. 6% by weight of a polyoxyethylene ether or ester surfactant;
  - vi. 5% by weight of glyceryl monostearate; and
  - vii. water, Wherein (A) total weight of the composition in the pump device is about 25 gm to about 50 gm, (B) the pump device delivers a unit dose amount of about 200-600 mg of the topical composition per actuation, more preferably about 300-500 mg of the topical composition per actuation and (C) at least 90% of the labelled concentration of mupirocin, more preferably at least 95% of the labelled concentration of mupirocin, is found after three months at 40° C. (±2° C.) and 75% (±5%) relative humidity (RH).

The percentages for the topical pharmaceutical compositions described herein are based on the total weight of the composition unless otherwise indicated. The topical pharmaceutical composition may also include minor amounts (such as up to 10%) of additives, such as viscosity modifiers, for example xanthan gum, and preservatives, such as phenoxyethanol or benzyl alcohol, including any combination of any of the foregoing. The composition may also include one or more buffering agents to maintain a suitable pH.

It should be understood by those versed in this art that the pump device as shown in FIG. 2 can be pre-filled with any suitable topical mupirocin pharmaceutical composition, such as a cream, an ointment, a lotion, a balm, or a salve, that can be effectively dispensed therefrom without departing from the purpose or scope of the present invention. Thus, when the pump device is described as being pre-filled with a topical mupirocin pharmaceutical cream, such description is done so for exemplary purposes without the intent to be bound to any particular topical mupirocin dosage form or formulation.

It is envisioned that in certain embodiments the pump device includes a take-up piston which is slidably disposed within the substantially tubular main body portion so as to partially define the storage chamber. The take-up position moves axially towards the pumping device when the pumping device is manually operated, so as to reduce the volume of the fluid storage chamber by an amount which is equivalent to the volume of the topical pharmaceutical composition dispensed from the dispensing system, i.e., the unit dose amount. In constructions wherein the take-up piston defines a portion of the storage chamber, it can be positioned during assembly to established the desired volume of the storage chamber. For example, if it is desired to pre-fill the dispensing device with 15 g of mupirocin cream, the piston can be initially positioned during the filling operation at a distance from the top of the main body portion of the dispensing package such that the volume of the fluid storage chamber corresponds to the volume required to hold 15 g of mupirocin cream. Alternatively, if 7.5 grams of cream is to be stored, the piston can be moved the appropriate distance towards the top of the main body portion of the dispensing package to accommodate 7.5 g of mupirocin cream. Of course, it should be appreciated by those versed in this art that the mupirocin pump device of the present invention contemplate functional storage chambers that can accommodate any desired volume of topical pharmaceutical composition, so long as the objectives of the present invention are not defeated.

Another embodiment is a dispensing system for treating secondarily infected traumatic skin lesions due to susceptible isolates of *Staphylococcus aureus* (*S. aureus*) and *Streptococcus pyogenes* (*S. pyogenes*) which includes, inter alia, a dispensing system that is pre-filled with a topical mupirocin pharmaceutical composition, such as a mupirocin cream. The dispensing system includes a pump device comprising a lower subassembly and an upper subassembly. The lower subassembly has a tubular body portion that defines an elongated interior storage chamber into which a take-up piston element is slidably disposed. The upper subassembly is mounted upon the lower subassembly and includes a dispensing head and an airless pumping mechanism. The dispensing head has an internal fluid passage or discharge duct formed therein which terminates in a outlet. The dispensing head also includes a finger-operated actuator which is operatively associated with the airless pumping mechanism. The dispensing package may further include a cap to seal or cover the dispensing head or nozzle.

The topical mupirocin pharmaceutical composition, e.g., mupirocin cream, is disposed at least partially within the storage chamber defined in the tubular body portion of the lower subassembly of the dispensing package. Operation of the finger-operated actuator causes the airless pumping mechanism to withdraw a portion of the mupirocin cream from within the interior chamber and to dispense the mupirocin cream into the internal fluid passage formed thereby discharging a predetermined final unit dose of mupirocin cream from the dispensing head.

In certain preferred embodiments, the take-up piston is disposed within the tubular body portion so as to partially define the storage chamber. The take-up position is arranged such that it moves axially towards the pumping device when the pumping device is manually operated, so as to reduce the volume of the storage chamber by an amount which is equivalent to the volume of mupirocin cream dispensed from the dispensing package, i.e., the unit dose amount, as discussed above.

In another embodiment, the pump device has a substantially tubular main body portion and a manually-operated airless pumping mechanism mounted on the main body portion. The main body portion of the pump device defines a storage chamber which is in fluid communication with a dispensing duct which is defined in the pumping device and that terminates in a discharge orifice.

More particularly, FIG. 1 illustrates an exploded view of a lower sub-assembly of a pump device, including a piston 1 and a container 2. The piston 1 and container 2 are made of materials compatible with the pharmaceutical formulation contained and dispensed, materials such as silicon, thermoplastic polyurethane (TPU), thermoplastic elastomer (TPE), low density poly ethylene (LDPE), polypropylene or other suitable polymer or elastomeric polymer materials.

An outer perimeter of the piston 1 is configured to fit snugly (by friction fit), within an inner diameter of the container 2, so to form a seal there between, while remaining slidably movable therein. In certain aspects, the piston 1 may contain an upper and/or lower lip, made of flexible material, radially extending slightly beyond a main, tubular portion of the piston 1.

Upon actuation of the pumping device, the piston 1 moves axially within the container 2, towards the pumping device, thereby reducing a volume of the storage chamber of the container 2 by an amount equivalent to a volume of pharmaceutical formulation dispensed from the pumping device. This take-up action of the piston 1, ensuring that the storage chamber of the container 2 is completely full of pharmaceutical formulation (i.e., no air), facilitates a precise unit dose volume with each actuation of the pumping device.

FIG. 2 illustrates an exploded view of an upper sub-assembly of a pump device, including a cap 1, an actuator 2, a valve 3, an inner actuator 4, a reduction plug 5, a bellow 6, an adaptor 7 and an adaptor ring 8. Similar to the components of the lower sub-assembly of the pump device, the components of the upper sub-assembly are made of materials compatible with the pharmaceutical formulation contained and dispensed, materials such as silicon, thermoplastic polyurethane (TPU), thermoplastic elastomer (TPE), polypropylene or other suitable polymer or elastomeric polymer materials.

The adaptor 7 and adaptor ring 8 configure a top of the container 2 to the main components of the manual, airless pumping mechanism (i.e., the actuator 2, valve 3, inner actuator 4, reduction plug 5 and bellow 6). An inner dispensing duct is defined by and within the actuator 2, inner actuator 4, reduction plug 5 and bellow 6, and includes the valve 3. A discharge orifice 14 is included in the actuator (dispensing head) 2. The cap 2 covers the pumping device and engages the adaptor 7.

The actuator (or dispensing head) 2 includes a finger operated button 16 (or actuator) operatively associated with the airless pumping mechanism. The actuator 2 resides over and about an outer circumference 18 of the inner actuator 4. The reduction plug 5 resides within the inner actuator 4, and has an outer upper lip 20 that abuts an inner upper shoulder 22 of the inner actuator 4. A lower shoulder 24 of the reduction plug 5 abuts an upper rim 26 of the bellow 6. The reduction plug 5 also includes a stem 28 that extends axially, from the lower shoulder 24 of the reduction plug 5, into the bellow 6.

The bellow 6 resides primarily within the adaptor 7. A lower shoulder 30 of the bellow 6 rests atop, and remains fixed relative to, a lower inner shoulder 32 of the adaptor 7. The bellow 6 includes a lower opening 34, below the lower shoulder 30 of the bellow 6, accessing an interior compartment 36 (pump chamber) of the bellow 6. The lower opening 34 of the bellow 6 accesses the pharmaceutical formulation of the storage chamber of the container 2, to draw pharmaceutical formulation from the storage chamber into the bellow 6.

During actuation of the pumping mechanism, depressing the finger operated button 16 of the actuator 2 results in downward axial movement of the inner actuator 4, which in turn similarly moves the reduction plug 5 against the upper rim 26 of the bellow 6. Downward movement of the upper rim 26 of the bellow 6 collapses the bellow 6, due to the stationary lower shoulder 30 of the bellow 6. The collapsing movement of the bellow 6 decreases a size of the interior compartment 36 (pump chamber) of the bellow 6, thereby forcing product from within the pump chamber 36 through dispensing duct and out the discharge orifice 14.

Actuation of the pumping mechanism may be stopped when the bellow 6 is completely collapsed. Alternatively, stops may be configured about or within the bellow 6 to limit the amount of actuation, all to better govern a precisely measured unit dose. Further, the volume of the dispensing duct, and/or the design of the reduction plug 5 can be strategically configured to direct a precisely measured unit dose.

Upon release of the actuation force, the bellow 6 springs back to an at-rest shape. The valve 3 may be configured to seal the dispensing duct and pump chamber 36, thereby forming a suction force that pulls product from the storage chamber of the container 2 into the lower opening 34 of the bellow 6. This suction force, drawing product from the storage chamber, also axially draws the floating, slidable piston 1 upward within the container 2, thereby reducing a volume of the storage chamber of the container 2. In an embodiment, the dimension of the opening orifice of the actuator (or dispensing head) is about 3.45 mm×1.75 mm.

The present invention is also directed to method for treating skin lesions (including secondarily infected traumatic skin lesions due to susceptible isolates of *Staphylococcus aureus* (*S. aureus*) and *Streptococcus pyogenes* (*S. pyogenes*)) with the dispensing system pre-filled with a topical mupirocin pharmaceutical composition. One embodiment is a method for treating secondarily infected traumatic skin lesions due to susceptible isolates of *Staphylococcus aureus* (*S. aureus*) and *Streptococcus pyogenes* (*S. pyogenes*) in a patient in need thereof comprising applying to the patient the topical mupirocin pharmaceutical composition dispensed from the mupirocin dispensing system of the present invention. In one embodiment, the topical mupirocin pharmaceutical composition is applied in accordance with an effective treatment regimen, such as one of those treatment regimens described herein. For example, the method may comprise (1) actuating a primed dispensing system pre-filled with a topical mupirocin pharmaceutical composition (such as one of those described herein) to dispense there from an effective precisely measured unit dose amount of the topical mupirocin pharmaceutical composition, wherein the unit dose amount dispensed per each actuation is the same effective precisely measured unit dose amount for consistent dose application over the course of the treatment, and (2) applying the dispensed unit dose amount to a treatment area.

Another embodiment is a method of applying a topical mupirocin pharmaceutical composition with a dispensing system comprising an airless pump device to a patient in need thereof where said method comprises (1) actuating a primed dispensing system pre-filled with a topical mupirocin pharmaceutical composition (such as one of those described herein) to dispense there from an effective precisely measured unit dose amount of the topical mupirocin pharmaceutical composition and (2) applying the dispensed unit dose amount to a treatment area on the patient.

The pump device may be primed by actuating the pump one or more times, such as 2 to 5 times, such as 2, 3, or 4 times.

The topical pharmaceutical composition may be prepared by:
 a. adding xanthan gum (e.g., over a period of time for 10-30 minutes) in water (e.g., purified water) in a container under stirring to form a clear dispersion (referred to as a the aqueous phase);
 b. heating mineral oil, polyox 20 cetostearyl ether and glyceryl monostearate (and then, for example, transfer oil phase to main manufacturing vessel and stir);
 c. adding mupirocin or a salt thereof (e.g., mupirocin calcium) to the oil phase to form a uniform dispersion;
 d. adding the aqueous phase to the oil phase (e.g., which is under stirring in main manufacturing vessel, and rinse the container with purified water to main manufacturing vessel and continue stirring); and
 e. optionally homogenizing and cooling the bulk and fill in suitable container.

The dispensing system of the present invention uniquely affords a proper, safe, convenient, easy and advantageous way to dispense and apply topical mupirocin pharmaceutical compositions to improve patient compliance and to more effectively treat secondarily infected traumatic skin lesions due to susceptible isolates of *Staphylococcus aureus* (*S. aureus*) and *Streptococcus pyogenes* (*S. pyogenes*), while mitigating, if not eliminating, the drawbacks associated with the use of aluminium tubes containing topical mupirocin formulations.

The following examples are provided to enable one skilled in the art to practice the invention and are merely illustrative of the invention. The examples should not be read as limiting the scope of the invention

EXAMPLES

Example 1

TABLE 1

| Mupirocin cream composition | |
|---|---|
| Components | % w/w |
| Mupirocin calcium dihydrate | 2.365 |
| Benzyl alcohol | 1.0 |
| Mineral oil | 50.6 |
| Phenoxyethanol | 0.5 |
| Xanthan gum | 0.215 |
| Cetomacrogol 1000 | 6.0 |
| Glyceryl monostearate | 5.0 |
| Purified Water | q.s. |

The mupirocin cream composition may be prepared as follows.

Step 1: Preparation of Aqueous/Oil/Drug Phase

Aqueous Phase
 Add xanthan gum in purified water under stirring to form a clear dispersion.

Oil Phase
 Heat mineral oil, cetomacrogol 1000 (polyoxyl 20 cetostearyl ether) and glyceryl monostrearate.
 Add benzyl alcohol and phenoxyethanol in the above phase.
 Transfer oil phase to main manufacturing vessel and stir.

Drug Phase
 Add the mupirocin calcium dihydrate to the oil phase to form a uniform dispersion.

Step 2: Add the aqueous phase to the oil phase in main manufacturing vessel and mix. Rinse the container with purified water.

Step 3: Homogenize and cool the bulk. Fill the bulk in a suitable container.

Example 2

The stability of the composition shown in Example 1 in the pump device was determined using HPLC (Column Inertsil C8, 250×4.6 mm, 5μ with detection at 240 nm). The results are shown in Table 2 below. It was observed that the stability of the mupirocin cream in the pump device was satisfactory.

TABLE 2

Stability data of Mupirocin Cream (Example 1) in Pump device

| | % Assay of Mupirocin | | | | | | |
|---|---|---|---|---|---|---|---|
| | | 25° C./60% RH | | | 40° C./75%RH | | |
| Device | Initial | 1 month | 2 month | 3 month | 1 month | 2 month | 3 month |
| Pump | 115.24 | 115.1 | 114.6 | 114.1 | 109.0 | 105.5 | 98.4 |

Example 3

A study was performed to determine the amount of mupirocin cream provided per actuation of the pump. The results are provided in Table 3 below.

TABLE 3

Actuation study of Mupirocin Cream from Pump (unit dose amount from pump per actuation)

| Mupirocin Cream Composition (from Example 1) | Quantity |
| --- | --- |
| Min. Amount delivered/Actuation | 0.342 Gram |
| Max. Amount delivered/Actuation | 0.447 Gram |
| Average Amount delivered/Actuation | 0.429 Gram |

The invention claimed is:

1. A mupirocin cream dispensing system comprising
   a. a topical cream composition comprising:
      i. 2.365% by weight of mupirocin or a salt thereof;
      ii. 1% by weight of benzyl alcohol;
      iii. 50.6% by weight of a mineral oil;
      iv. 0.5% by weight of phenoxyethanol;
      v. 0.215% by weight of xanthan gum;
      vi. 6% by weight of a polyoxyethylene ether or ester surfactant;
      vii. 5% by weight of glyceryl monostearate; and
      viii. water; and
   b. a pump device comprising a dispensing head having an internal fluid passage formed therein which terminates at an outlet; an actuator; a valve; an inner actuator; a reduction plug; and a bellow; where the internal fluid passage is further defined within the actuator, the inner actuator, the reduction plug, the bellow, and the valve; and where: the actuator resides over and about an outer circumference of the inner actuator; the reduction plug resides within the inner actuator, and has an outer upper lip that abuts an inner upper shoulder of the inner actuator; a lower shoulder of the reduction plug abuts an upper rim of the bellow; and the reduction plug includes a stem extending axially, from the lower shoulder of the reduction plug, into the bellow;
   wherein said pump device delivers a unit dose amount of about 300 to about 500 mg of topical cream composition per actuation.

2. The mupirocin cream dispensing system according to claim 1, wherein a total weight of said topical cream composition in said pump device is in a range of about 25 gm to about 50 gm.

3. The mupirocin cream dispensing system according to claim 1, wherein said topical cream composition is prepared by steps comprising:
   (a) adding xanthan gum to purified water to form an aqueous phase;
   (b) heating a mixture of mineral oil, polyoxyl 20 cetostearyl ether and glyceryl monostearate to form an oil phase;
   (c) adding benzyl alcohol and phenoxyethanol to the oil phase;
   (d) adding mupirocin or a salt thereof to the oil phase to form a uniform dispersion; and
   (e) adding the aqueous phase to the oil phase which to form the topical cream composition.

4. The dispensing system of claim 1, wherein: the bellow resides primarily within the adaptor; a lower shoulder of the bellow rests atop, and remains fixed relative to, a lower inner shoulder of the adaptor; and the bellow includes a lower opening, below the lower shoulder of the bellow, accessing an interior pump chamber of the bellow; the lower opening of the bellow accesses the topical cream composition in a storage chamber of the pump device, to draw the topical cream composition from the storage chamber and into the bellow.

5. The dispensing system of claim 4, wherein the pump device is configured so that, during actuation, depressing a finger operated button of the actuator results in downward axial movement of the inner actuator, which in turn similarly moves the reduction plug against the upper rim of the bellow; where downward movement of the upper rim of the bellow collapses the bellow, due to the stationary lower shoulder of the bellow; and where collapsing movement of the bellow decreases a size of the interior pump chamber of the bellow, thereby forcing the topical cream composition from within the interior pump chamber of the bellow, through the internal fluid passage, and out of the dispensing head.

6. The dispensing system of claim 5, wherein the pump device is configured so that, upon release of the finger operated button, thereby releasing actuation force, the bellow springs back to an at-rest shape, wherein a suction force forms that pulls the topical cream composition from the storage chamber into the lower opening of the bellow.

\* \* \* \* \*